United States Patent [19]
Khatri

[11] Patent Number: 4,535,254
[45] Date of Patent: Aug. 13, 1985

[54] TOUCH-OPERATED POWER CONTROL DEVICE

[75] Inventor: Dilip K. Khatri, Miranda, Australia

[73] Assignee: Electrical Equipment Limited, Sydney, Australia

[21] Appl. No.: 492,025

[22] PCT Filed: Aug. 26, 1982

[86] PCT No.: PCT/AU82/00140
§ 371 Date: Apr. 22, 1983
§ 102(e) Date: Apr. 22, 1983

[87] PCT Pub. No.: WO83/00780
PCT Pub. Date: Mar. 3, 1983

[30] Foreign Application Priority Data
Aug. 26, 1981 [AU] Australia ................. PF0436

[51] Int. Cl.³ ............................................. H02J 3/14
[52] U.S. Cl. .................................. 307/38; 307/114;
307/115; 307/140; 340/825.19
[58] Field of Search .................. 307/38, 40, 114, 115,
307/116, 126, 140, 141, 41, 113; 340/815.14,
815.15, 825.19; 361/166–169.1; 455/164, 165

[56] References Cited
U.S. PATENT DOCUMENTS

| | | | |
|---|---|---|---|
| 3,416,001 | 12/1968 | Fistell | 307/38 |
| 3,704,422 | 11/1972 | Thomson | 455/164 |
| 3,719,828 | 3/1973 | Lipskin | 307/115 |
| 3,854,055 | 12/1974 | Sparko | 307/115 |
| 4,156,193 | 5/1979 | Baker | 455/165 X |
| 4,282,422 | 8/1981 | Payne et al. | 307/40 X |

OTHER PUBLICATIONS

Patient Breath Pulse Control System for Operating Various Electrical Devices, by R. P. Sapp, Western Electric Tech. Digest, No. 54, 4-1979.

Primary Examiner—Harry E. Moose, Jr.
Assistant Examiner—Derek S. Jennings
Attorney, Agent, or Firm—Ladas & Parry

[57] ABSTRACT

A power switching device especially for use by handicapped persons for remote power switching by an operator of available appliances, comprising a touch sensor producing a first signal and a second signal with a successive touch, cycling control means including a clock oscillator responding to the first signal to cause identified display of the appliances in continuing sequence, and a circuit responding to the second signal to halt identifying the sequence at a selected display and to switch power to the appliance corresponding to the selected display either on if not already on or off if already on.

7 Claims, 12 Drawing Figures

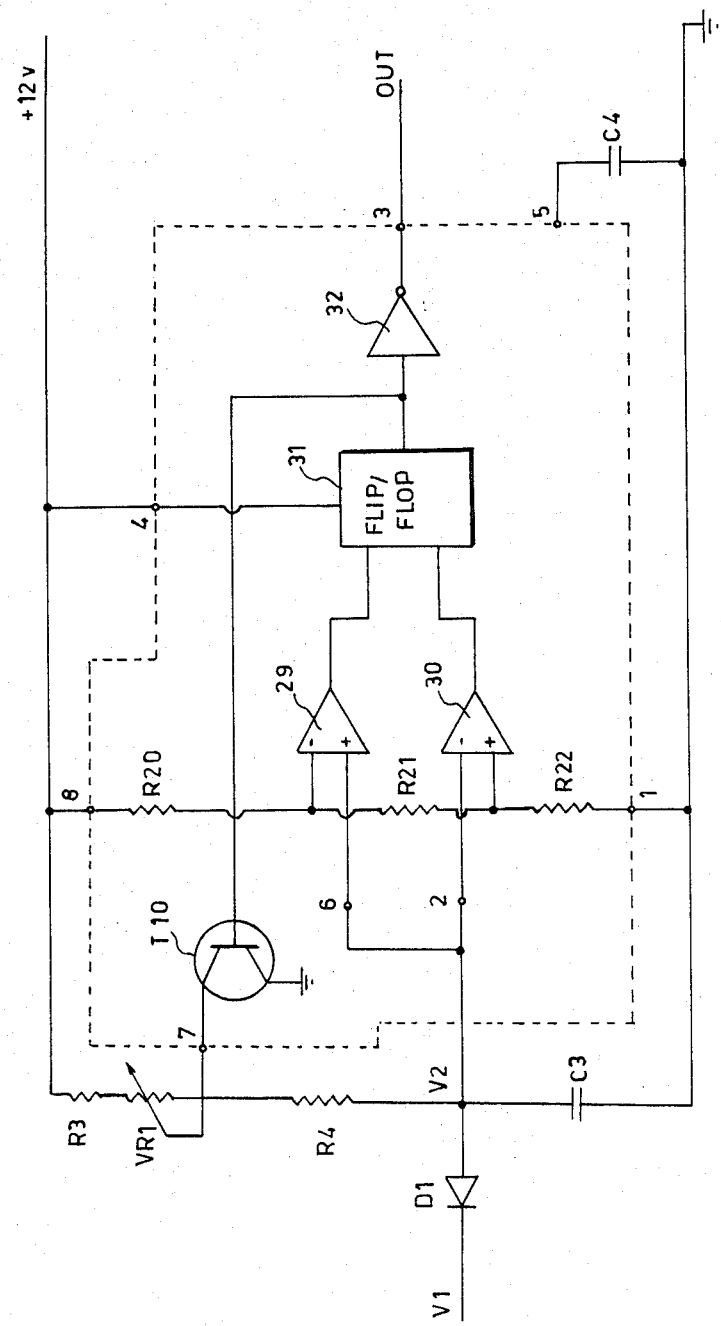
F I G. 4

TOUCH-OPERATED POWER CONTROL DEVICE

This invention relates to electric-power control devices having facility for selection of power connection to multiple outlets, and more particularly to a device of this kind which is made responsive to operator-touch.

BACKGROUND ART

An ideal application of this device is for use by the disabled where a person frequently desires to select for operation an electrical appliance, or facility, from several available to him. For example there may be such facilities available as an electric lamp, radiator, radio, television, and even a "nurse call" alarm. If individual controls or switches, are provided for his use confusion can arise, especially for a mentally retarded patient.

It is the principal object of the invention to provide a power control device responsive to operator-touch and which is simple to operate and functions reliably.

DISCLOSURE OF INVENTION

According to a general form of this invention there is provided a selective power control device for the connection of electric power from a source to a selected one of a plurality of power lines associated with individual electrical functions or appliances, comprising a presentation to the operator of the functions or applicances available to him, operator-controlled sensor means, means responsive to a first signal from said sensor means to initiate a successive identification to said operator of individual ones of said functions or appliances, means responsive to a second signal from said sensor means to halt said successive identification at a selected one of said functions or appliances, and means to switch on power from said source to said power line associated with said selected one of said functions or appliances.

BRIEF DESCRIPTION OF DRAWINGS

The invention will now be described in more detail with reference to the accompanying drawings, in which:

FIG. 4 shows schematically the construction of the power supply circuit;

BEST MODE OF CARRYING OUT THE INVENTION

Figure 1B:
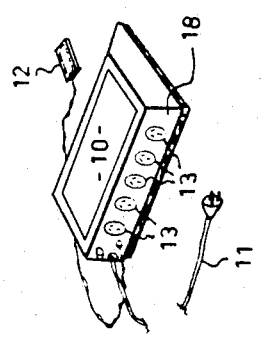
FIGS. 1A and 1B show respectively a front perspective, and a rear perspective on a smaller scale, of the cabinet of a power control device according to this invention.
Figure 1A:
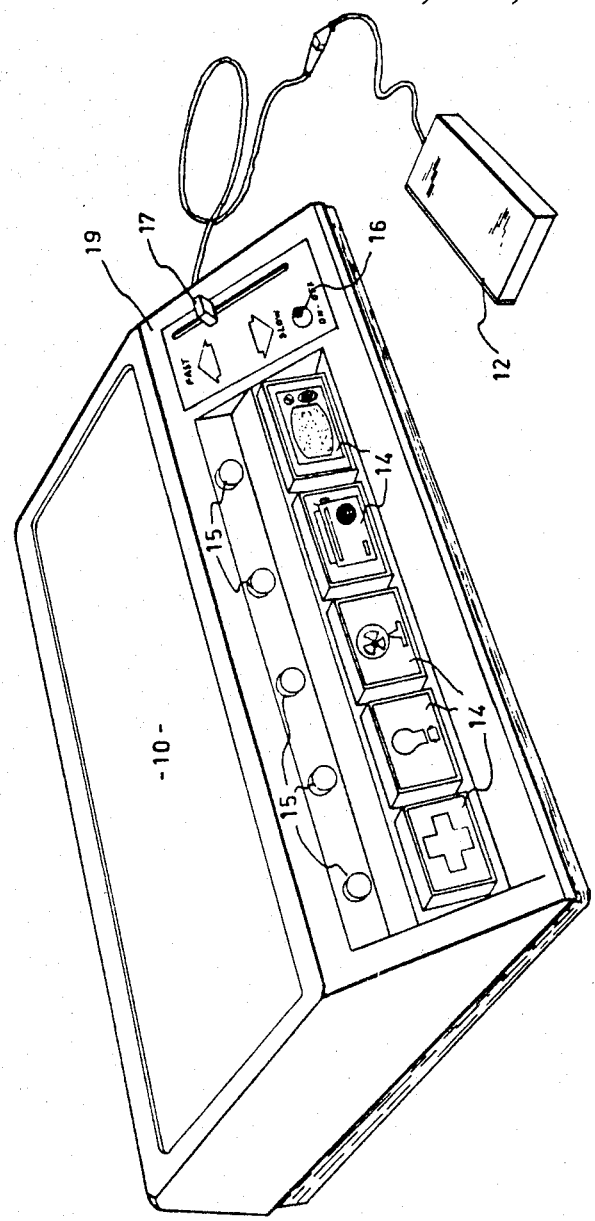
Figure 2:
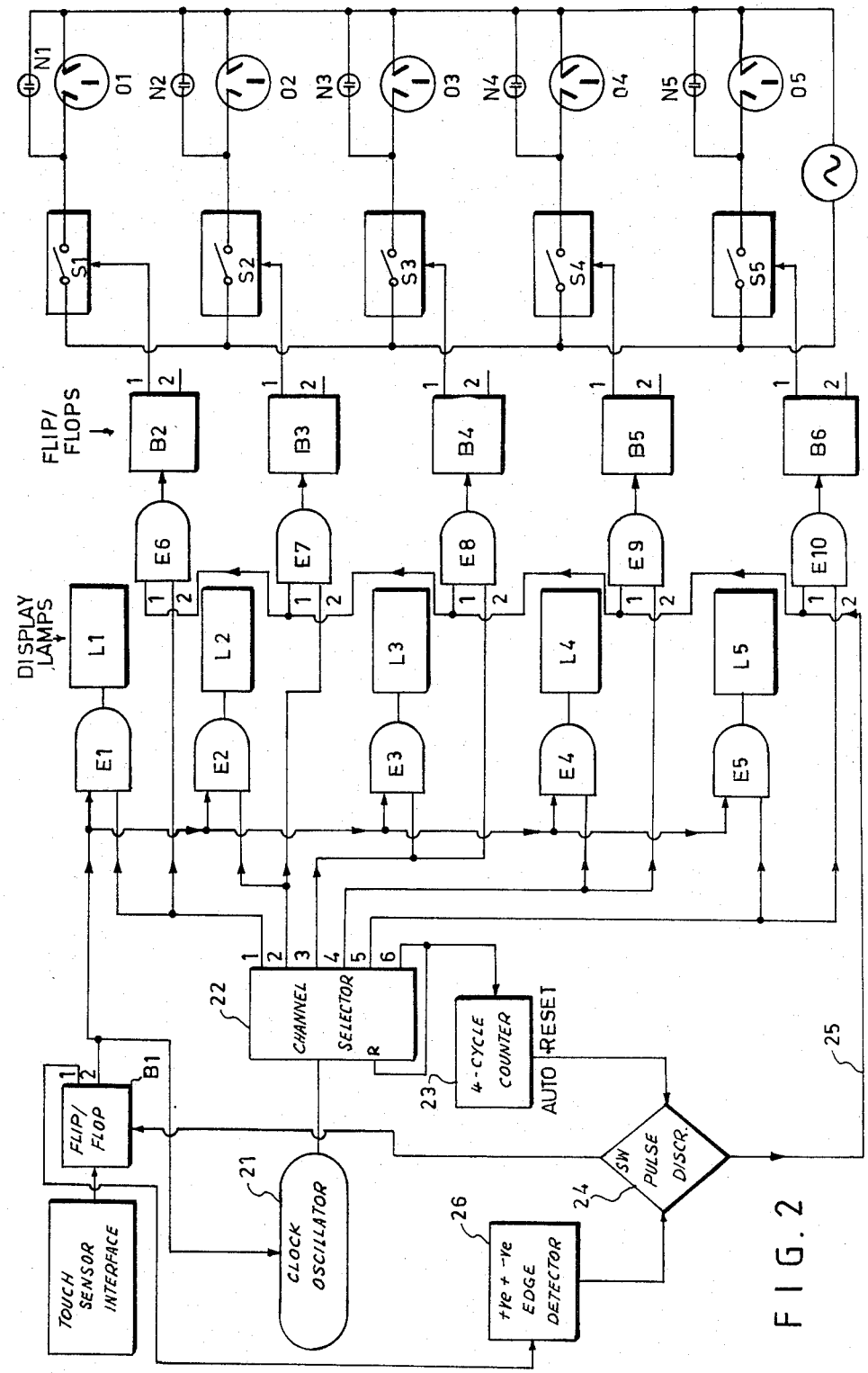
FIG. 2 is a block diagram of the circuit of the power control device.

The selective power control device of the invention is housed within a cabinet 10 such as shown in FIGS. 1 and 2. A power cable 11 for connection to a power source (not shown) is connected to electronic circuitry within the cabinet 10 and an operator's touch sensor device 12 is plugged into the rear 18 of the cabinet 10. A row of power sockets 13 are arranged at the rear 18 of the cabinet 10 into which may be inserted the power plugs of respective electrical appliances (not shown). A row of function panels 14 with corresponding overhead neon indicators 15 are arranged along the front 19 of the cabinet 10. The functions as shown, which may be varied, are in order "nurse call", light, fan, radio and television. Each of the panels 14 includes an interior lamp for illumination in turn during cycling of the individual functions as will become clear from the following description. An ON-OFF power button 16 and a selector-speed slide control 17 are also accessible to the operator at the front 19 of the cabinet 10.

The electronic circuit within cabinet 10 is shown generally by the clock diagrammatic representation of the power control device shown in FIG. 2. A touch interface 20 controls a divide-by-two flip-flop circuit B1 in such a manner that at successive touches of the sensor 12, the output 1 of B1 goes alternately high (+12v) and low (0v). These two states at the output of B1 correspond to two distinct phases of the circuit operation as follows: phase 1 serves for channel cycling where output 1 of B1 is high, and output 2 of B1 is low, while phase 2 is for channel on-off switching control when the output 1 of B1 is low and the output 2 of B1 is high. Therefore, at the initial touch by the operator and all succeeding odd-numbered touches, the state of the circuit is as follows: output 1 of circuit B1 is high which activates the clock oscillator 21. Pulses from the clock output are counted by a channel selector stage 22 whose 5 outputs correspond to 5 individual channels by which power to individual appliances is controlled. Other decade counters with longer counts may be used if more than 5 switching functions are required. Only one of the channel selector outputs is high at any one time, and when it is high that channel is selected to energize the corresponding display by lamps in the function panel 14 (see FIG. 1A), i.e. if say output 2 is high then lamp L2 becomes illuminated which would in FIG. 1 correspond to say the room light function panel 14. Under these conditions output 2 of circuit B1 is low whereby input 1 of all of the and gates E6 to E10 are placed low. The channels, therefore, are cycled by the recurring count in channel selector 22 and the lamps behind panels 14 are lit successively to indicate to the operator the channel choice available to him at that instant. If no further touch is recorded on the sensor 12, the channel selector 22 will continue to cycle through until its output 6 goes high for the fourth time at which point an auto-reset stage, via its 4-cycle counter 23, becomes effective. When an auto-reset signal is received at the end of the fourth selection cycle a signal is produced via the switch pulse discriminator 24 to reset circuit B1 to the stand-by mode, i.e. with its output 1 high and output 2 low. The switch pulse discriminator 24 prevents this auto-reset signal being transmitted over the ON-OFF control bus 25. Output 2 of circuit B1 is normally low, however during phase 2, which will be referred to later, output 2 of circuit B1 goes from low to high and a positive-going edge is detected by the edge detector unit 26 and transmitted over the ON-OFF bus. During phase 1 when output 2 of circuit B1 goes from high to low the negative-going edge is detected by the unit 26 and no signal is allowed to pass through the switch pulse discriminator 24 to the ON-OFF control bus 25.

Concerning phase 2 of the circuit operation, upon the second touch of the sensor 12 the circuit B1 reverses its outputs so that output 1 goes low to stop the clock oscillator 21 thereby causing the channel selector 22 to halt its count and de-energises the display lamps L1 to L5 via and gates E1 to E5. Simultaneously, output 2 of the circuit B1 goes high sending all of the inputs 1 of and gates E6 to E10 also high. Now as both inputs 1 and 2 of gate E7 are both high, its output also goes high. The rising edge of this transition clocks the flip-flop B3 and as can be seen the remaining flip-flops B2 and B4 to B6 are not clocked in this condition as their inputs 2 are all low. As output 2 of circuit B3 changes from low to high it causes power switch S2 to close and apply power to outlet 02, while neon N2 (indicator 15 of FIG. 1A) becomes illuminated to indicate that channel 2 is energized. If, however, output 2 of flip-flop B3 had changed from high to low then the reverse would have happened, i.e. switch S2 would have gone open to interrupt power to the outlet 02 and indicator neon N2, with channel 2 then being de-energized. Hence, due to the transitionary action of the edge detector 26, described in more detail hereafter, switching from power on to power off, and vice-versa, occurs alternately with each even-numbered touch providing that the same channel is selected. If, of course, different channels are selected, with each even-numbered touch ultimately all of the functions available would be switched on.

The reason for the de-energisation of the display lamps L1 to L5 should now become clear. If, for instance, power output on channel 2 had been turned off and the display was not de-energised, the corresponding lamp L2 would have been illuminated to mislead the operator. De-energisation of the display also serves as an indication that the circuit is in a stand-by mode ready to pass back into phase 1. If, for example, channel 2 had been turned off, and channel 1 is required to be energized, the procedure would be to touch the sensor 12 once and wait until lamp L1 is illuminated, then touch again so that channel 1 becomes energized. It will become clear from the following description of the clock oscillator that a delay occurs in the oscillator before pulses are produced and this delay can be found to enable the operator to touch again to switch off power on the selected channel before cycling re-commences.

As an accessory to the control device a feature incorporating control of intensity of power supplied at the respective outlet 01 to 05 may be included. For instance, upon even-numbered touches if the operator's contact with the sensor 20 is maintained the output voltage may be varied incrementally, or even continuously, by the response in known fashion of an integrated circuit such as presently available chip S576 marketed by Siemens Ag of West Germany.

DETAILED DESCRIPTION OF CIRCUITRY

Figure 3A:
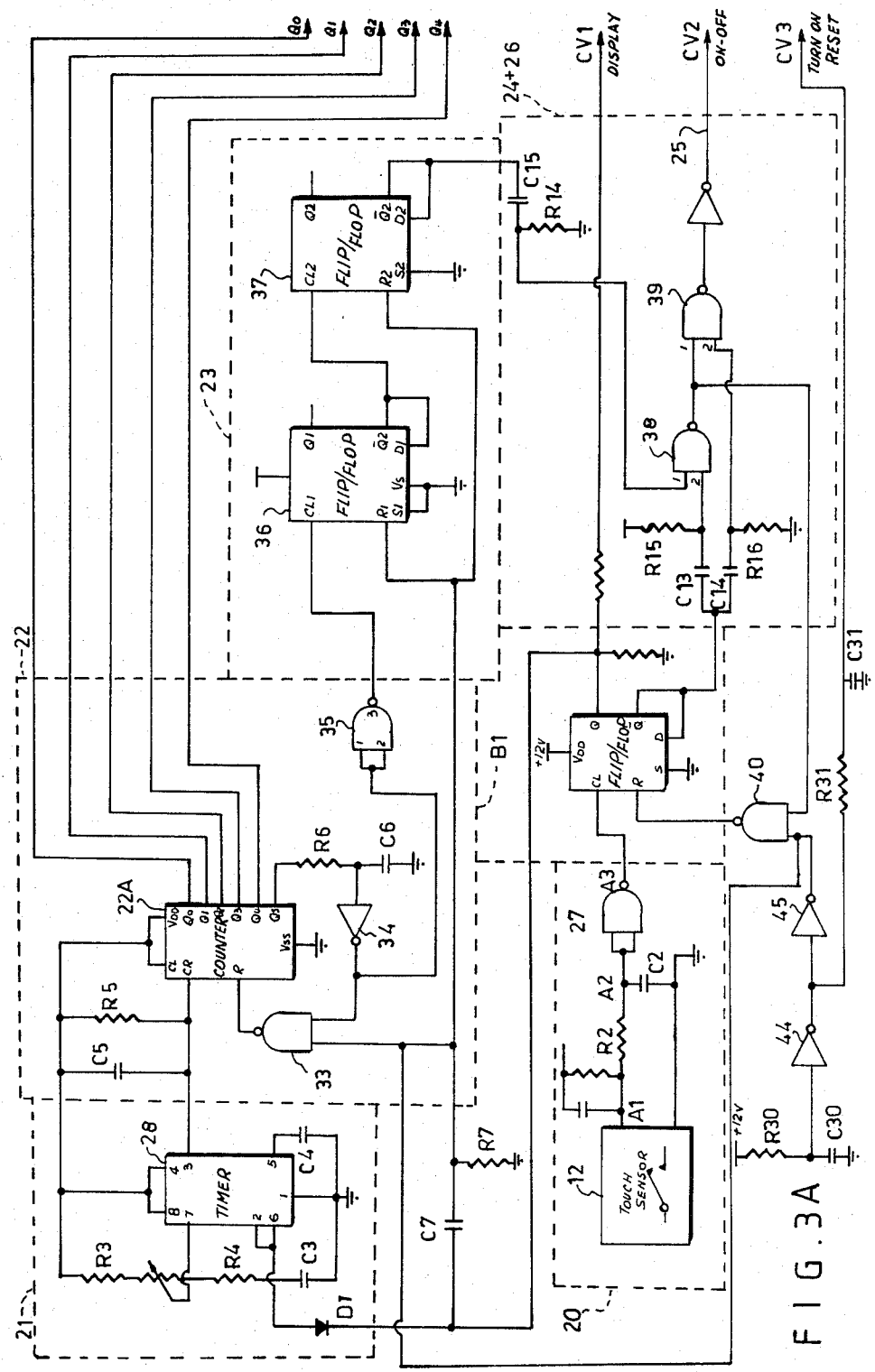
FIGS. 3A and 3B together depict a detailed schematic drawing of the circuit of said device.
Figure 3B:
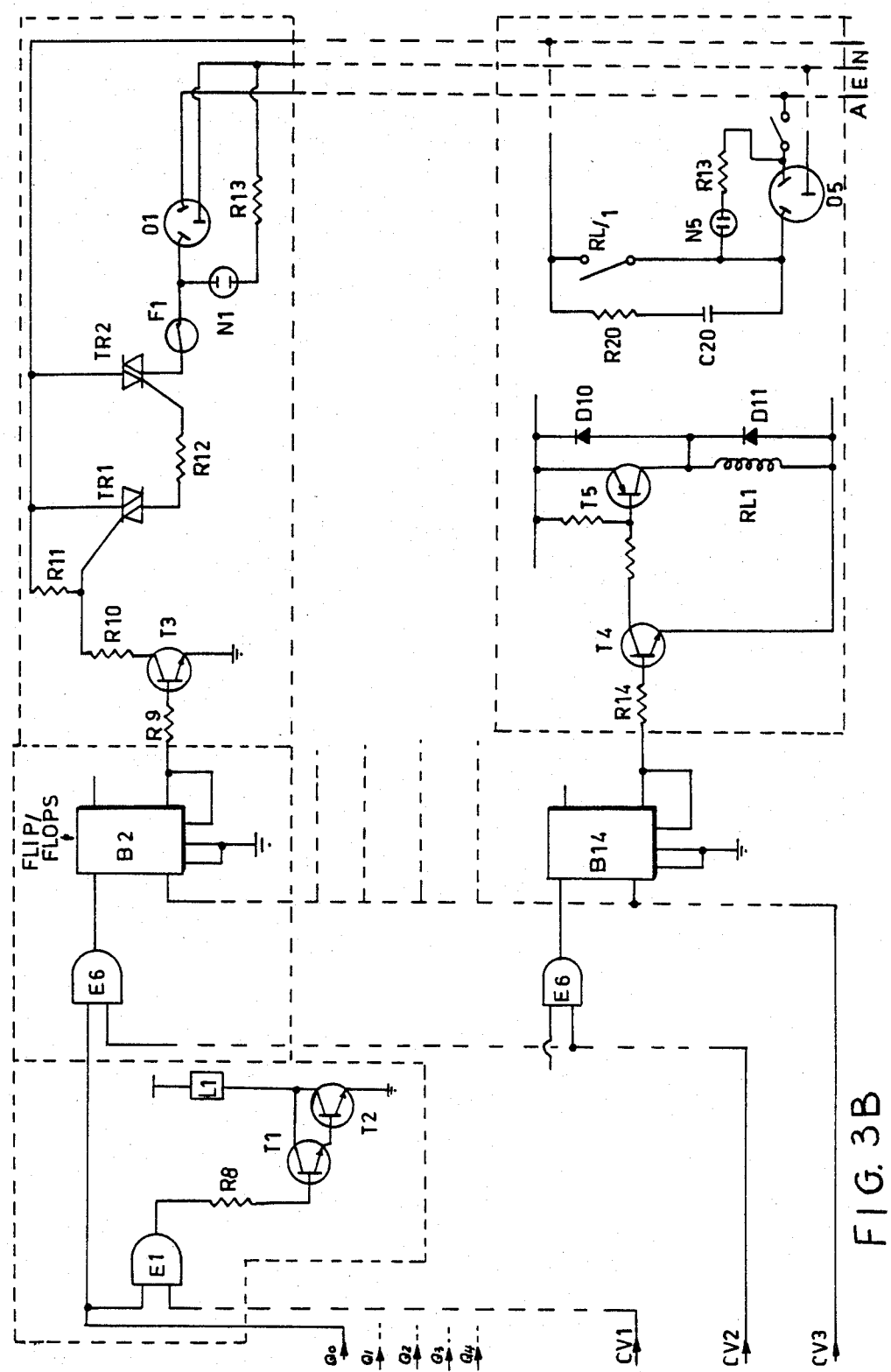

Reference is now made to FIGS. 3A and 3B for a more detailed description of the circuitry of this invention. In the "untouched" condition of sensor 12, points A1 and A2 are high while A3 is low. When the sensor 12 has been touched the wave forms at A1 and A2 are as shown in FIG. 5B of the drawings. Resistor R2 and capacitor C2 form a low pass filter for the Schmitt Trigger inverter 27 which squares-up the wave form from points A2 to A3. Thus a fast rise-time positive transition is obtained when the sensor 12 is touched.

The divide-by-two circuit B1 is a flip-flop connected in the toggle mode, where the Q output leads the D output. At successive pulses from the touch interface circuit 20 the Q output alternately goes high and low. These two states correspond to two distinct phases of the circuit operation, viz. high in the case of channel cycling and low in the case of channel on-off switch control.

Figure 7A:
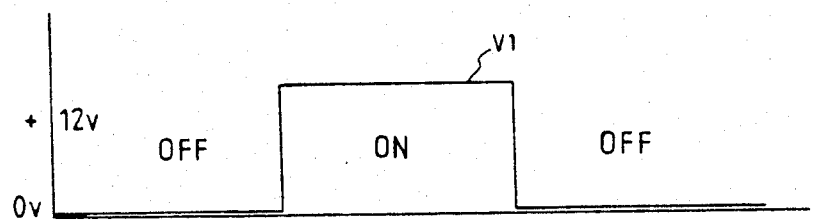
FIGS. 7A, 7B and 7C show wave forms associated with the clock oscillator.
Figure 7B:
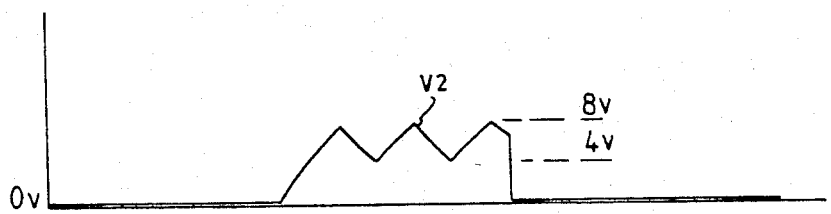
Figure 7C:
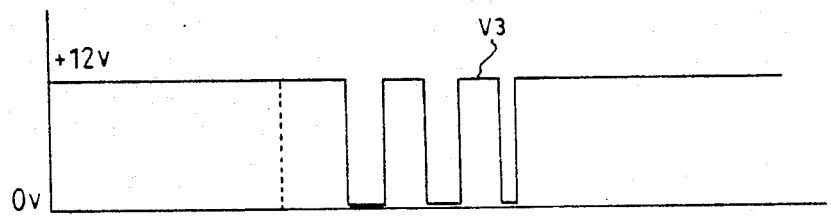

The clock oscillator circuit 21 consists of an ICM7555 low power timer chip 28 which is connected as an astable multivibrator. The frequency and mark/space ratio are provided by resistors R3, R4 and VR1 (corresponding to the control 17 of FIG. 1A) and capacitor C3. Capacitor C4 decouples pin 5 to ground. The equivalent circuit of the chip 28 is shown in FIG. 4 and it contains a 3-resistor potential divider R20, R21 and R22, two voltage comparators 29 and 30, a flip-flop 31, a transistor T10 and an output buffer 32. The divider ratios are such that $\frac{1}{3}$ of the supply voltage (i.e. 4v) is set on the lower comparator 30 and $\frac{2}{3}$ of the supply voltage (i.e. 8v) is set on the upper comparator 29. The circuit action is such that, in each operating cycle, capacitor C3 first charges up to 8v through resistors R3, R4 and VR1, at which point the upper comparator 29 activates the flip-flop 31 and turns the internal transistor T10 on. The transistor T10 then discharges capacitor C3 through resistor R4 until the capacitor C3 voltage falls to 4v, at which point the lower comparator 30 activates the flip-flop 31 and turns the internal transistor T10 off to cause capacitor C3 to recharge through resistors R3, R4 and VR1. The operating cycle is then complete and repeats ad infinitum. A ramp waveform with an amplitude that swings between 4v and 8v is generated across capacitor C3 and a rectangular wave form is generated at the output pin 3. The clock oscillator wave forms are shown in FIGS. 7A, B and C. FIG. 7A shows the gating voltage V1 from circuit B1, FIG. 7B shows voltage V2 at capacitor C3 and FIG. 7C shows the output voltage V3. The oscillator is gated on or off by diode D1. When the circuit is gated on, diode D1 is back-biased and the astable operates in the normal way, but when the circuit is gated off, diode D1 shorts out capacitor C3 and pulls voltage V2 to ground. It should be noted that when the astable is gated on, the first half cycle is again considerably longer than the succeeding half cycles, but that the capacitor C3 voltage falls abruptly to zero at gate-off. Furthermore, the output is high in the off state.

The channel selector 22 consists basically of a 4017 CMOS counter chip 22A. Only one of its outputs is high at any time. When power is applied, the circuit is reset across the network of resistor R7, capacitor C7, and Dual Input Nand Schmitt Trigger 33. The output $Q_o$ then goes high when a negative transition is applied to the clock enable input CE, $Q_1$ goes high and $Q_o$ low. This sequence continues until $Q_5$ goes high and a second reset circuit is initiated. This includes resistor R6, capacitor C6 and Schmitt Trigger Inverter 34. Consequently $Q_o$ then goes high again and the cycle is repeated while resistor R5 and capacitor C5 prevent spurious clocking. The auto-reset circuit 23 (FIG. 2) is "clocked" at the end of each selection cycle, i.e. the transition of Q5 from low to high is detected at the output of gate 35 which feeds the 4-cycle counter 23 composed of two flip-flops 36 and 37. The 4-cycle counter is energised by the clock-start signal from the Q output of circuit B1. At the end of the fourth cycle $\overline{Q}_2$ of circuit 37 goes high which, via the switching signal discriminator 24, is able to reset circuit B1. Hence, the clock oscillator is disabled and the system reverts to the stand-by mode. If phase 2 is initiated before the fourth cycle is reached, the auto-reset counter 23 is stopped until phase 1 is re-activated and the clock oscillator 21 is re-started. The auto-reset counter 23 is initialised again by the "clock-start" signal from the Q output of circuit B1, and the above procedure is repeated.

During operation of the device a visual indication of the channels selected is required and this is achieved by the channel display units (FIG. 33), each composed of an AND gate such as any one of gates E1 to E5, cascaded transistors T1 and T2 and one of lamps L1 to L5. For simplicity only one of these circuits and associated channels is shown and each circuit functions in a similar manner, such as gate E1 has its input 1 connected to terminal $Q_o$ of the channel selector 22, and its input 2 connected to receive control voltage CV1 from the Q output of circuit B1. During the channel cycling phase of the circuit output Q is high so that if output $Q_o$ is also high then the output of gate E1 is also high. Thus current will flow through resistor R8 to saturate transistors T1 and T2 to cause lamp L1 to light thereby indicating that channel 1 is available in the cycle. If either output Q or $Q_o$ is low then the output of gate E1 is also low and transistors T1 and T2 as well as lamp L1 are in an off condition.

It is necessary for each channel to contain a circuit able to decide whether the power should be On or Off and this is achieved by the channel on-off control logic which for each channel is composed of one of the AND gates E6 to E10 and an associated one of the divide-by-two circuits B2 to B6. Input 1 of gate 38 of the circuit 24,26 (FIG. 3A) is normally low, except when an auto-reset signal is received. Gate 38 and resistor-capacitor R15-C13 form the negative edge trigger network 26. When $\overline{Q}$ of circuit B1 goes from high to low, the negative edge is produced at input 2 of gate 38. Since input 1 of gate 38 is normally low, the output thereof will remain high as will that of gate 39. Also as input 2 of gate 38 is normally low, no change is observed at the output of gate 39. Inputs 1 and 2 of gate 40 are high and hence its output is low. However, when $\overline{Q}$ of circuit B1 goes from low to high during phase 2, a positive-going edge is produced on input 2 of gate 39. Since input 1 of gate 39 is normally high, an output pulse is produced at the output as a result of the positive edge. This output pulse is transmitted as a control voltage CV2 along the on/off control bus 25 to the channel on/off control logic circuits and is shown for simplicity in FIG. 3B as connected to gates E6 and E10.

During auto-reset input 1 of gate 38 is normally low. When an auto-reset signal is received at the end of the fourth selection cycle, a positive pulse is applied to input 1 of gate 38. Since input 2 is normally high, a negative edge pulse is generated at the output of gate 38 which is used to reset circuit B1 via gate 40. Since input 2 of gate 39 is normally low, the pulse signal at the output of gate 38 is blocked from being transmitted down the ON-OFF control bus 25. When circuit B1 is reset its Q output goes from high to low, which stops the clock oscillator 21 and the display is disabled.

The circuit from the 12V supply via resistor R30 and bypass capacitor C30 and inverter 44 supplies an initial reset pulse, upon application of power to the device, to circuit B1 via inverter 45 and to circuits B2 to B6 via a filter represented by resistor R31 and capacitor C31.

Each of the first four channels has a solid state power switch S1 to S4, rated at 500 Watts, which is driven from the channel on-off control logic. These power switches S1 to S4 are identical. When the output from circuit B2 is high, current will flow through resistor R9 to saturate transistor T3 and permit gate current to flow through Triac TR1 via resistor R10. Resistor R11 protects the gate junction of the sensitive gate TR1, which triggers TR2 via resistor R12 and hence power is supplied to the outlet 01. Under these conditions neon N1 lights up via the current limiting resistor R13. The Triacs TR1 and TR2 are protected by a fuse F1. When the input is low the reverse will occur so that no current flows into resistor R9 hence transistor T3 and Triacs TR1 and TR2 are in an off condition and the supply of power to outlet 01 is interrupted. The neon N1 indicates this condition by turning off. It will be noted that Triacs TR1 and TR2 form an amplifying gate Triac system known as a "TRIWAG". Power is derived from the active, earth and neutral lines A, E, N.

The fifth channel or switch S5, is utilized for driving heavy duty or inductive loads and switching is achieved by a 10 amp relay RL1. Input for the relay driver comes from the previous on-off control logic. When the input is high current flows through resistor R14 to saturate transistors T4 and T5 and their output current flows in relay coil RL1 to close its contacts. Power is then applied to the outlet 05 and the neon N5 lights via the current limiter R13. Diodes D10 and D11 protect the transistor T5 from voltage transients. When the input is low the reverse will occur, i.e. no current flows in resistor R14 so that transistors T4 and T5 are off and no excitation current flows in the relay RL1 so that its contacts remain open. Power is therefore switched off and the neon is not illuminated. A spark quench circuit of resistor R20 and capacitor C20 is connected over contacts RL/$_1$.

The power supply 41 is a full-wave rectified type using a bridge BR1 and with a transformer TS1 and a zener diode regulator ZN1. The two outputs are 15 volts unregulated at 200 mA and 12 volts regulated at 10 mA. The high current supply drives the lamps L1 to L5 and the relay coil RL1 while the low current supply drives the low power CMOS circuitry. Diode D6 provides the power on-off indication for the power control device. Capacitors C21, C22 and C23 form a delta house suppression network.

Figure 5A:
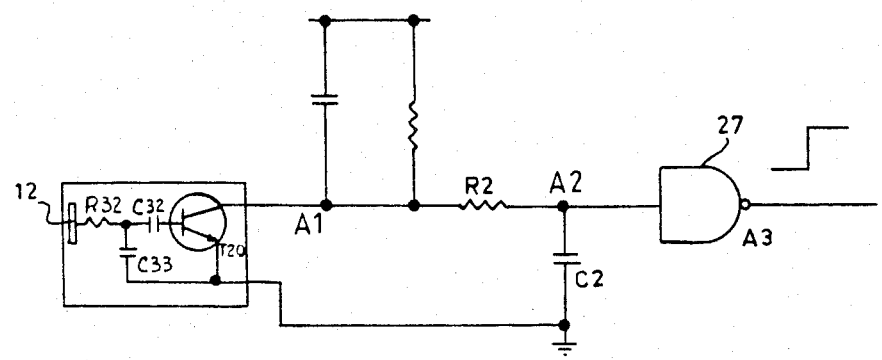
FIGS. 5A and 5B depict the circuit of the touch sensor and wave forms occurring therein.
Figure 5B:
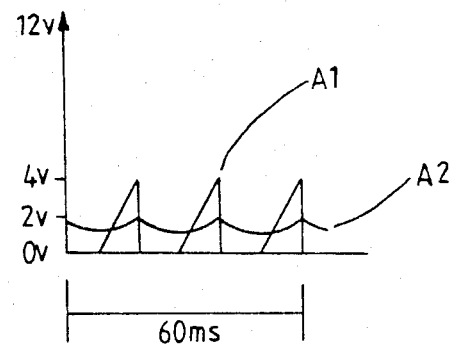
Figure 6:
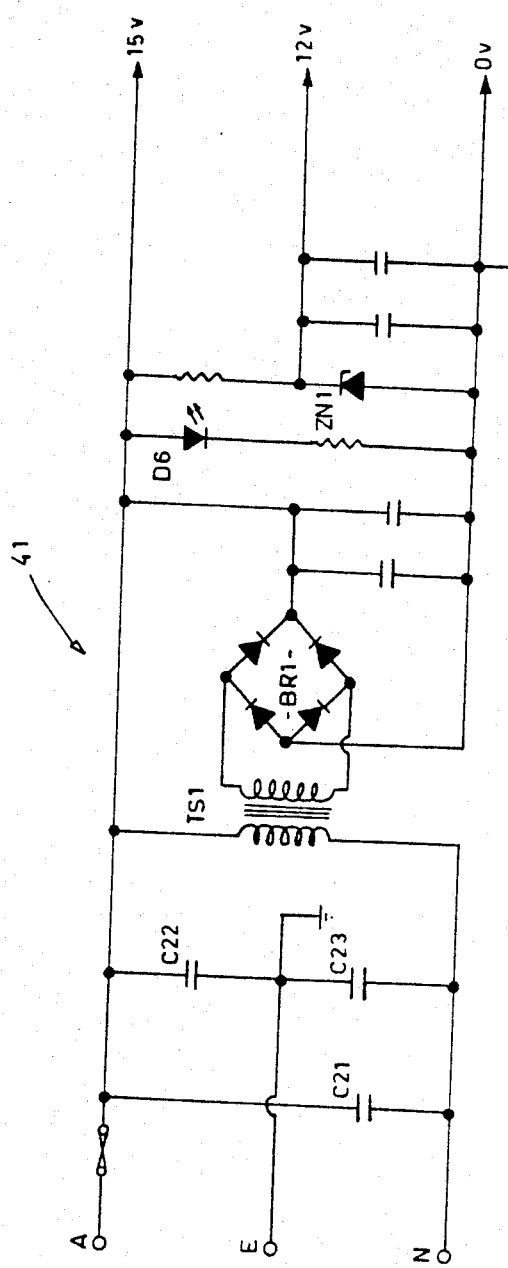
FIG. 6 is a schematic drawing of the clock oscillator.

The general form of the touch sensor unit is shown in more detail in FIG. 5A. 50 Hz hum is received by the sensor plate 12 upon operator body contact and is applied through resistor R32 and capacitors C32 and C33, forming a low-pass high-pass filter, to the switching transistor T20 which is saturated during the presence of a signal and at cut-off when a signal is not present.

Whereas a preferred embodiment has been described in the foregoing passages it should be understood that other forms, embodiments and modifications are possible within the scope of this invention.

I claim:
1. A selective power control device for the connection of electric power from a source to a selected one of a plurality of power lines associated with individual electrical functions or appliances, comprising a visual display to the operator of the functions or appliances available to him, operator-controlled sensor means, cycling control means including a clock oscillator responsive to a first signal from said sensor means to initiate repeated cycling providing an automatic successive identification to said operator of individual ones of said functions or appliances, means responsive to a second signal from said sensor means to halt said successive identification at a selected one of said functions or appliances, switches for controlling power application to said power lines, an electronic counter having a plural outputs connected to respective ones of said switches to switch on power from said source to said power line associated with said selected one of said functions or appliances, and an auto-reset counter connected to an output of said electronic counter to de-energise said clock oscillator after cycling through a predetermined number of repetitions.

2. A power control device according to claim 1, wherein said first and said second signals are generated by said sensor means alternately with successive touches by the operator, and said switching means also responds to receipt of said second signal.

3. A power control device according to claim 2, wherein when said switching means has switched on said power, response to the next received second signal causes said switching means to switch off said power.

4. A power control device according to claim 1, wherein said selected one of said functions or appliances is that one of the available functions or appliances identified to the operator at the instant when said second signal is generated by operation of said sensor means.

5. A power control device according to claim 1, wherein said sensor means is responsive to the touch of the operator to generate a pulse with each touch which triggers a bistable device from one condition to another so as to produce said first and said second signals corresponding to a respective one of said conditions.

6. A power control device according to claim 1, further comprising an enclosing cabinet having a plurality of power sockets for plugging-in of said appliances, and wherein said presentation of said functions or appliances is a visual display on said cabinet and said successive identification is achieved by lamp illumination, and said sensor means is an operator-touch pad remote from said cabinet.

7. A selective power control device for the connection of electric power from a source to a selected one of a plurality of power lines associated with individual electrical functions or appliances, comprising a presentation to the operator of the functions or appliances available to him, operator-controlled sensor means, means responsive to a first signal from said sensor means to initiate repeated cycling providing a successive identification to said operator of individual ones of said functions or appliances, said initiation means comprises cycling control means including a clock oscillator energised by receipt of said first signal and an electronic counter having plural outputs connected to respective ones of switches controlling power application to said power lines means responsive to a second signal from said sensor means to halt said successive identification at a selected one of said functions or appliances, means to switch on power from said source to said power line associated with said selected one of said functions or appliances and an auto-reset counter connected to an output of said electronic counter to de-energise said clock oscillator, after cycling through a predetermined number of repetitions.

* * * * *